United States Patent [19]

Nakano et al.

[11] Patent Number: 4,694,809

[45] Date of Patent: Sep. 22, 1987

[54] METHOD AND SYSTEM FOR INTERNAL COMBUSTION ENGINE OXYGEN SENSOR HEATING CONTROL WITH TIME SMOOTHING

[75] Inventors: Jiro Nakano; Takao Ishibashi; Takao Akatsuka; Masao Kawaguchi, all of Toyota, Japan

[73] Assignee: Toyota Jidosha Kabushiki Kaisha, Aichi, Japan

[21] Appl. No.: 898,783

[22] Filed: Aug. 15, 1986

Related U.S. Application Data

[63] Continuation of Ser. No. 666,466, Oct. 30, 1984, abandoned.

[30] Foreign Application Priority Data

May 7, 1984 [JP]  Japan .................................. 59-90881

[51] Int. Cl.$^4$ ........................ F02M 51/00; F02M 7/00; G01V 27/26; C25B 1/24
[52] U.S. Cl. .................................. 123/489; 123/440; 204/425; 204/1 T
[58] Field of Search ........................ 123/489, 440, 494; 204/195 S, 406, 425, 424, 427, 429, 1 T; 73/23

[56] References Cited

U.S. PATENT DOCUMENTS

| | | | |
|---|---|---|---|
| 4,332,225 | 6/1982 | Cox et al. | 123/440 |
| 4,354,468 | 10/1982 | Sone et al. | 123/440 |
| 4,365,604 | 12/1982 | Sone | 123/440 |
| 4,440,621 | 4/1984 | Kitahara et al. | 123/489 |
| 4,462,366 | 7/1984 | Nomura et al. | 123/489 |
| 4,464,244 | 8/1984 | Uchida et al. | 204/425 |
| 4,471,648 | 9/1984 | Uchida et al. | 73/23 |
| 4,528,961 | 7/1985 | Katoh et al. | 123/489 |

*Primary Examiner*—Raymond A. Nelli
*Attorney, Agent, or Firm*—Kenyon & Kenyon

[57] ABSTRACT

An internal combustion engine has an exhaust system and an oxygen sensor fitted to the exhaust system including a sensor element and an electrically powered heater for heating the sensor element. A method is disclosed for controlling the power supplied to the heater by determining a target value therefor according to engine operational parameters, by applying a smoothing correction to the target value to produce an actual value, and by supplying power to the heater in an amount according to this actual power value. The smoothing may be done by time-smoothing, and may be done by performing the calculation repeatedly in a cycle and by setting the actual power value amount equal to a function of this target power value and of values of this actual power value amount determined in previous cycles. This function may take the form of a weighted average, and as a special case such a weighted average may use only the actual power value amount determined in the previous cycle. Accordingly it is ensured that the heater is properly operated even in the case of quick variation in the engine operational parameters, which due to system inertia will only alter the exhaust gas temperature with a certain time lag. Thus, the oxygen sensor is properly kept heated up, even in such quick engine operational state alteration conditions, and engine performance and the quality of exhaust gas emissions at such a time are ensured to be good. A system is also described for implementing this method.

5 Claims, 9 Drawing Figures

INITIALIZATION SUBROUTINE
- REGISTER INITIALIZE
- DEFINE I/O PORTS

BASE SUBROUTINE
- CALCULATE FUEL INJECTION AMOUNT AND WATER TEMPERATURE CORRECTION COEFFICIENT FOR FUEL INJECTION AMOUNT

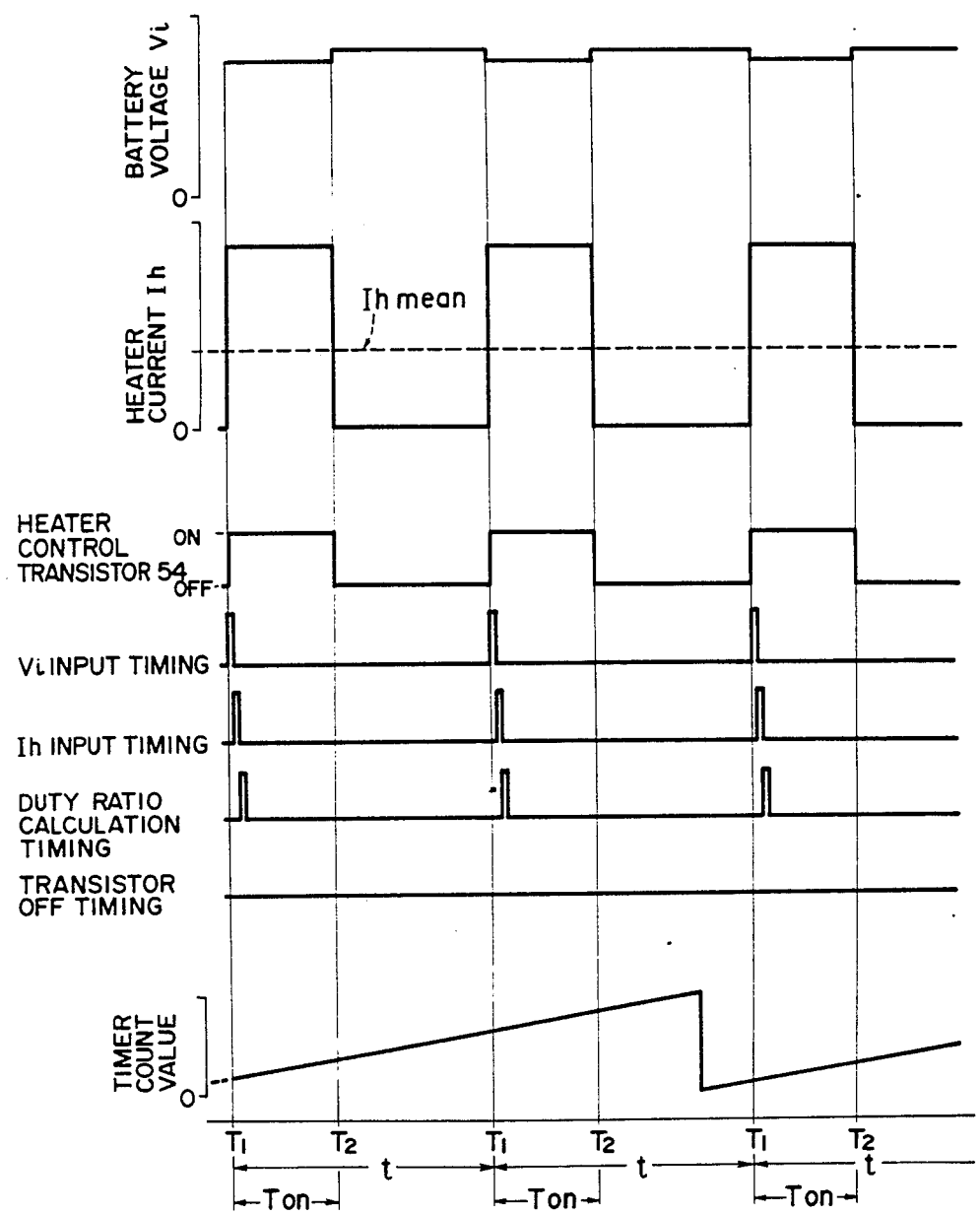

METHOD AND SYSTEM FOR INTERNAL COMBUSTION ENGINE OXYGEN SENSOR HEATING CONTROL WITH TIME SMOOTHING

This application is a continuation of application Ser. No. 666,466, filed Oct. 30, 1984, now abandoned.

BACKGROUND OF THE INVENTION

The present invention relates to a method of controlling the heating of an oxygen sensor fitted to the exhaust system of an internal combustion engine for the purpose of controlling air-fuel mixture air/fuel ratio, and to a system for practicing the method. More particularly, the present invention relates to such a method and device for oxygen sensor heating control which perform a time smoothing and time delaying of the power dissipated in a resistive electrical heater element of the oxygen sensor, so as to ensure that the oxygen sensor is kept at a proper temperature even when engine operational parameters change at a high rate.

It is known to fit an oxygen sensor to the exhaust system of an internal combustion engine. Such an oxygen sensor typically comprises a solid electrolyte or semiconductor, and varies a generated current or resistance in response to the concentration of oxygen in the exhaust gases of the engine. This electrical signal is fed to a control device which controls the amount of fuel provided to the engine in relation to the amount of air sucked thereinto, and is used for controlling the air/fuel ratio of the air-fuel mixture supplied to the engine by a feedback process. Various such forms of control device, which practice various methods of air-fuel mixture ratio control, are per se known.

The output of the sensor element of such an oxygen sensor varies with temperature, and, particularly when the air/fuel ratio is weak and is in the range of 17 to 25, in order for the sensor element to accurately measure the oxygen concentration, said sensor element must be maintained at a temperature higher than a certain critical minimum active temperature. This maintenance of the temperature of the sensor element can be done by using a heater, and oxygen sensors with sensor element heaters have already been proposed, along with methods for operation of such heaters; for example in Japanese Patent Application No. 53-78476, which has been published as Japanese Patent Application No. 54-13396. Further, in Japanese Patent Application No. 53-83120, which has been published as Japanese Patent Publication No. 54-21393, there has been proposed a method and a system for control of the electrical power supplied to such an oxygen sensor element heater, in which the power is varied as a function of intake manifold pressure, of throttle opening, and of engine revolution speed, so as to ensure that the oxygen sensor element is kept at a temperature no lower than its minimum active temperature.

The sensor element of such an oxygen sensor fitted to an exhaust system is of course heated up by the exhaust gases in the exhaust system, so the effect of a heater for the sensor element must be controlled to take account of the temperature of these exhaust gases. Now, in an internal combustion engine which is controlled by a throttle valve, the exhaust temperature is largely determined by the amount of air-fuel mixture supplied per engine piston stroke and by engine revolution speed, and if the air-fuel ratio of the air-fuel mixture is constant the amount of such mixture supplied is proportional to the rate of intake air flow. Therefore, in the above mentioned patent applications, the above are used as parameters, and the supply of electricity to the sensor element heater is varied depending on the engine load and the engine revolution speed. Thus, the exhaust temperature is considered to depend on the engine intake flow and engine revolution speed, and the values are determined experimentally in advance with reasonable accuracy. This method and system are adequate to keep the temperature of the sensor element of the oxygen sensor reasonably constant regardless of engine operational conditions, provided however that these engine operational condition do not change too abruptly.

However, when the operating parameters of the engine change abruptly, this method and system do not provide satisfactory operation. This is because the temperature of the exhaust gases does not react instantaneously to changes of the engine operating parameters, such as throttle opening, engine revolution speed, engine load, intake system pressure, intake system flow rate, and so on, but instead reacts with a certain characteristic time lag, which may be termed an inertial smoothing effect. If therefore as suggested above the operation of the oxygen sensor heater is controlled as a strict function of such engine operational parameters, then when the values of the relevant parameters change the amount of power that is being supplied to the oxygen sensor heater will accordingly be changed substantially simultaneously, and this will not be in accordance with the actual ongoing temperature of the exhaust gases. For example, if from a low load engine operating condition the accelerator pedal of the vehicle is stepped upon, which will in due course after the aforesaid time lag cause the temperature of the exhaust gases to rise, then according to such a system as above outlined the amount of power supplied to the oxygen sensor heater will immediately be reduced in anticipation of the aforesaid exhaust gas temperature rise, thus allowing the temperature of the oxygen sensor undesirably to drop, before the warming up thereof by the increase in temperature of the exhaust gases can take place. This will cause a temporary drop in the temperature of the oxygen sensor heater, which can be very troublesome, and can lead to poor operation of the air/fuel ratio control system, and to high levels of emission of pollutants in the exhaust gases of the engine as well as to poor engine operation and drivability. Likewise and conversely, if from a high load engine operating condition the accelerator pedal of the vehicle is released from being depressed, which will in due course after the aforesaid time lag cause the temperature of the exhaust gases to drop, then according to such a system as above outlined the amount of power supplied to the oxygen sensor heater will immediately be increased in anticipation of the aforesaid exhaust gas temperature drop, thus allowing the temperature of the oxygen sensor undesirably to rise, before the cooling down thereof by the drop in temperature of the exhaust gases can take place. This will cause a temporary rise in the temperature of the oxygen sensor heater, which can lead to overheating thereof and damage thereto. This phenomenon can also occur when the engine of the vehicle is stopped while the ignition switch thereof is left in the on condition (so called "hot soaking").

Both of these troublesome operational modes of the prior art are illustrated in FIGS. 8 and 9 of the accompanying drawings, which are mutually coordinated graphs showing, against time, various quantities relating both to the operation of an engine incorporating a prior art oxygen sensor heating system and to the operation of an engine incorporating an oxygen sensor heating system according to the present invention. In FIG. 8, the depression from idling position, and the restoration thereof, of the throttle pedal of the vehicle incorporating the engine are shown by the dip in the uppermost solid line, and the subsequent rise thereof, and the lines denoted by Pm, Ne, and Te represent respectively pressure in the engine intake system, engine revolution speed, and exhaust gas temperature. Thus, it is seen that the time points of the rise in the exhaust gas temperature and of the subsequent fall thereof are significantly delayed after the time points of the depression of the accelerator pedal and of the subsequent release thereof. Correspondingly, in FIG. 9, in the case of the prior art described above the time variation of the power supplied to the heater element is shown by the dashed line, and this is advanced in time with relation to the variation of the exhaust gas temperature Ts shown in FIG. 8, so that the temperature of the sensor element of the oxygen sensor, which is shown by the double dotted line, is quite high, first being a temperature drop when the accelerator pedal is depressed and then a temperature rise when the accelerator pedal is released again.

SUMMARY OF THE INVENTION

Accordingly, it is the primary object of the present invention to provide a method and system for internal combustion engine oxygen sensor heating control, which perform such control of the power supplied to the oxygen sensor heater, as to ensure that the oxygen sensor is kept at a proper temperature at all times.

It is a further object of the present invention to provide such a method and system for oxygen sensor heating control, which perform such a control of the oxygen sensor heater, as to ensure a proper temperature for the oxygen sensor, particularly when engine operational parameters change abruptly.

It is a further object of the present invention to provide such a method and system for oxygen sensor heating control, which perform such a control of the oxygen sensor heater, as to ensure a proper temperature for the oxygen sensor in substantially all engine operating conditions.

It is a further object of the present invention to provide such a method and system for oxygen sensor heating control, which avoid any risk that upon rapid increase of engine load the temperature of the sensor element should be allowed to drop.

It is a further object of the present invention to provide such a method and system for oxygen sensor heating control, which avoid any risk that upon rapid decrease of engine load the temperature of the sensor element should be allowed to rise.

It is a further object of the present invention to provide such a method and system for oxygen sensor heating control, which do not risk overheating the heater element of the oxygen sensor heater.

It is a further object of the present invention to provide such a method and system for oxygen sensor heating control, which do not place unnecessary stress on the heater element of the oxygen sensor heater, or damage thereto.

It is a yet further object of the present invention to provide such a method and system for oxygen sensor heating control, which maintains the reliability of the heater element of the oxygen sensor heater and of the apparatus as a whole.

It is a yet further object of the present invention to provide such a method and system for oxygen sensor heating control, which minimize the occurrence of the condition that during quick variation of operational parameters of the engine the quality of the exhaust emissions of the engine should be poor.

It is a yet further object of the present invention to provide such a method and system for oxygen sensor heating control, which minimize the occurrence of the condition that during quick variation of operational parameters of the engine the drivability of the engine should be poor.

It is a yet further object of the present invention to provide such a method and system for oxygen sensor heating control, which minimize the occurrence of the condition that during so called "hot soak" the oxygen sensor element should be unduly heated up.

According to the most general method aspect of the present invention, these and other objects are accomplished by, for an internal combustion engine comprising an exhaust system and an oxygen sensor fitted to said exhaust system comprising a sensor element and an electrically powered heater for heating said sensor element: a method for controlling the electrical supply to said heater, wherein: a target value for the power to be supplied to said heater is determined according to engine operational parameters; a smoothing correction is applied to said target value to produce an actual value for the power to be supplied to said heater; and power in an amount according to said actual power value amount is supplied to said heater; and, according to the most general apparatus aspect of the present invention, these and other objects are accomplished by, for an internal combustion engine comprising an exhaust system and an oxygen sensor fitted to said exhaust system comprising a sensor element and an electrically powered heater for heating said sensor element: a system for controlling the electrical supply to said heater, comprising: a means for determining a target value for the power to be supplied to said heater according to engine operational parameters; a means for applying a smoothing correction to said target value to produce an actual value for the power to be supplied to said heater; and a means for supplying power in an amount according to said actual power value amount to said heater.

According to such a method and such a system, by the smoothing performed on the target value of the power to be supplied to said heater, the effects of time delay in the response of exhaust gas temperature to change in the operational parameters of the engine are reproduced in the behavior of the power supplied to the heater, which is similarly time-delayed. Accordingly, according to this method and system, such control of the power supplied to the oxygen sensor heater is performed, as to ensure that the oxygen sensor is kept at a proper temperature at all times. In particular, such a control of the oxygen sensor heater is performed, as to ensure a proper temperature for the oxygen sensor, particularly when engine operational parameters change abruptly. Further, any risk is particularly avoided that upon rapid increase of engine load the temperature of the sensor element should be allowed to drop; and, similarly, any risk is particularly avoided that upon rapid decrease of engine load the temperature of the sensor element should be allowed to rise. Thus, no risk is run of overheating the heater element of the oxygen sensor heater, or of placing unnecessary stress on the heater element of the oxygen sensor heater, or of causing damage thereto. This, therefore, maintains the reliability of the heater element of the oxygen sensor heater and of the apparatus as a whole. Further, it is prevented that during quick variation of operational parameters of the engine the quality of the exhaust emissions of the engine should be poor, that the drivability of the engine should be poor, or that during so called "hot soak" the oxygen sensor element should be unduly heated up.

If as is preferable the above described calculation is performed repeatedly in a cycle, and the smoothing correction is performed by setting said actual power value amount equal to a function of said target power value and of values of said actual power value amount determined in previous ones of said cycles, then the time-smoothing may be simply and accurately performed; and if the function is a weighted average, then the calculation is easy. Further, if the weighted average is only of said target power value and of the value of said actual power value amount determined in the previous one of said cycles, then the calculation is even easier and quicker.

BRIEF DESCRIPTION OF THE DRAWINGS

The present invention will now be shown and described with reference to the preferred embodiment thereof, and with reference to the illustrative drawings. It should be clearly understood, however, that the description of the embodiment, and the drawings, are all of them given purely for the purposes of explanation and exemplification only, and are none of them intended to be limitative of the scope of the present invention in any way, since the scope of the present invention is to be defined solely by the legitimate and proper scope of the appended claims. In the drawings, like parts and features are denoted by like reference symbols in the various figures thereof, and:

FIG. 7 is a time chart showing, against time, the voltage being delivered by the battery of the vehicle incorporating this system, the current being supplied to the heater for the oxygen sensor element, the ON/OFF signal to a heater control transistor, a voltage input timing, a heater current input timing, the timing of a calculation of duty ratio, the timing of a transistor-OFF signal, and the value of a count C counted by a timer, in the case of this preferred embodiment of the present invention;

DESCRIPTION OF THE PREFERRED EMBODIMENT

Figure 1:
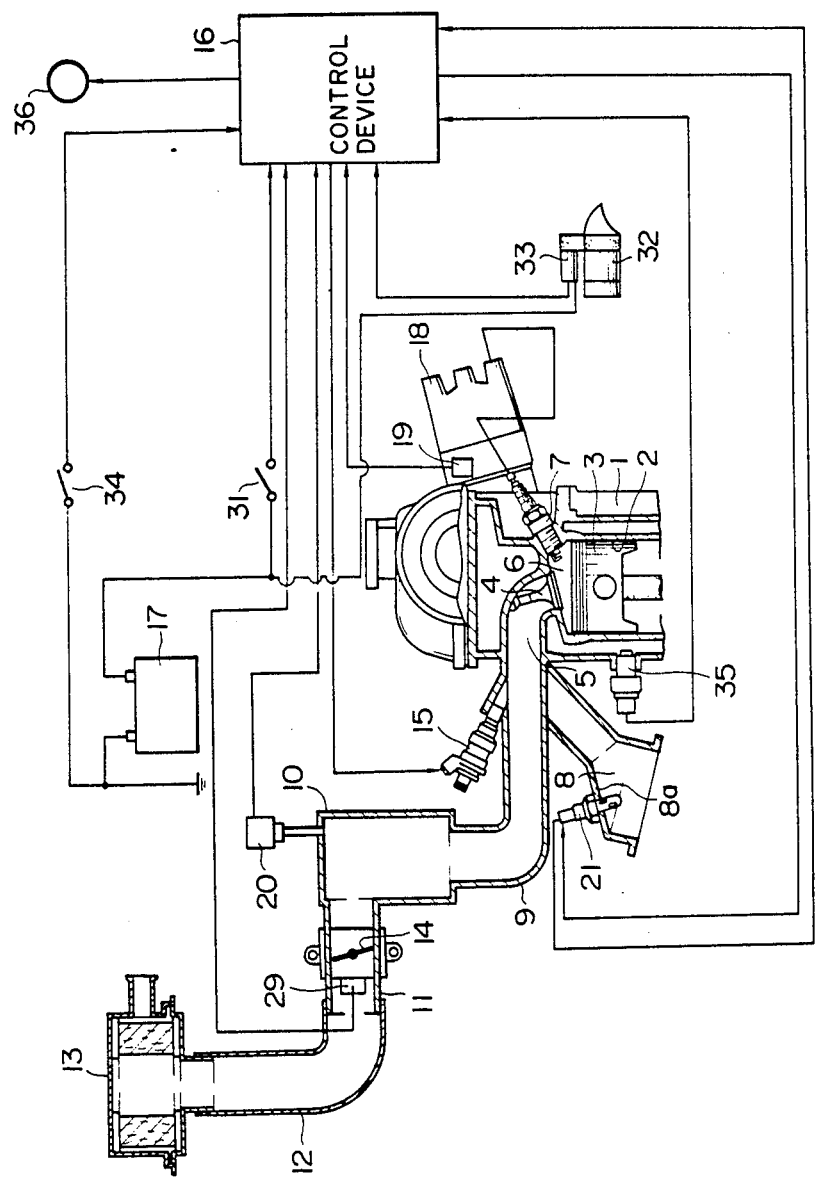
FIG. 1 is a partly schematic partly sectional view of an internal combustion engine which is equipped with the preferred embodiment of the oxygen sensor heating control system of the present invention, also showing various ancillary elements thereof.

FIG. 1 shows in schematic view an internal combustion engine with an oxygen sensor of the above described kind, said engine incorporating the preferred embodiment of the oxygen sensor heating control system of the present invention, for performing the preferred embodiment of the oxygen sensor heating control method of the present invention. In this figure, the internal combustion engine 1 has a cylinder bore 2 within which a piston 3 reciprocates, said piston 3 being coupled in a per se conventional manner to a crankshaft, now show, by a connecting rod, only partially shown; in fact the engine 1 has a plurality of such cylinders and pistons but only one of each of them can be seen in the figure. A combustion chamber 6 is defined above the piston 3 in the figure in the cylinder bore 2, between it and a cylinder head, and an intake port 5 opens to this combustion chamber 6 via a valve aperture the opening and closing of which is controlled by an intake valve 4. A per se conventional spark plug 7 provides ignition for air-fuel mixture in the combustion chamber 6 when appropriately energized. Further, an exhaust port, not shown in the figure, opens to the combustion chamber 6 via a valve aperture the opening and closing of which is controlled by an exhaust valve, also not shown, and to this exhaust port there is connected an exhaust system, only a portion of an exhaust manifold 8 incorporated in which is shown.

To the inlet port 5 there is connected the downstream end of an intake manifold 9, the upstream end of which is connected to the outlet of a surge tank 10. To the inlet of the surge tank 10 there is connected the downstream end of a throttle body 11, the upstream end of which is connected to the downstream end of an inlet tube 12. The upstream end of this inlet tube 12 is communicated to the outlet of an air cleaner 13, the inlet of which is left open to the atmosphere. In the throttle body 11 there is mounted an intake butterfly valve 14 the opening and closing action of which for intake air amount control is linked to the foot depression movement of a throttle pedal for the engine 1, not shown, by a throttle pedal linkage also not shown.

To the intake manifold 9 there is mounted a per se conventional fuel injection valve 15 which incorporates a solenoid 15a (not shown particularly in FIG. 1), and this fuel injection valve 15 is supplied with pressurized fuel (i.e. gasoline) by a fuel supply system which is not shown. The opening and closing action of this valve 15 is electronically controlled by a control device 16 which will be more particularly described hereinafter. Thus, the valve 15 squirts spirts of fuel into the intake manifold 9 the total volume of each of which depends on the opening and closing times thus provided for said fuel injection valve 15 by the control device 16.

The control device 16 is supplied with actuating electrical energy from the battery 17 of the vehicle to which this engine 1 is fitted, via an ignition switch 31. To the distributor 18 of the engine 1 there is fitted a crank angle sensor 19, the electrical output signal of which is representative of the position of the crankshaft of the engine 1 and is dispatched to the control device 16. To the surge tank 10 of the engine 1 there is fitted an intake pressure sensor 20, the electrical output signal of which is representative of the air pressure in the intake system of the engine 1 and is also dispatched to the control device 16. To the wall 8a of the exhaust manifold 8 of the engine 1 there is fitted an oxygen sensor 21 to be more particularly described later, the electrical output signal of which is representative of the oxygen concentration in the exhaust gases flowing through said exhaust manifold 8 and is also dispatched to the control device 16; and the oxygen sensor 21 further has a heater 28 as will be described later, supply of actuating electrical energy to which is provided from the control device 16. To the throttle valve 14 mounted in the intake system of the engine 1 there is fitted a throttle valve idling opening amount sensor 29 incorporating a switch 29a (not shown particularly in FIG. 1), the electrical output signal of which is also dispatched to the control device 16 and is representative of the opening amount of said throttle valve 14, being ON when said throttle valve 14 is opened by more than a predetermined amount and thus indicating engine operation at a level higher than idling level and being OFF when the throttle valve 14 is opened by less than said predetermined amount and thus indicating engine idling operation. To the starter 32 of the engine 1 there is fitted a starter switch 33, an electrical output signal from which is indicative of whether said starter 32 is being actuated to crank said engine 1 or not and is also dispatched to he control device 16. And to the water jacket of the engine 1 there is fitted a water temperature sensor 35, the electric output signal of which is indicative of the temperature of the cooling water of said engine 1 and is also dispatched to the control device 16. Further, a test switch 34 optionally provides earthing for a terminal of the control device 16, and an output signal from said control device 16 is fed to a test alarm lamp 36.

Figure 2:
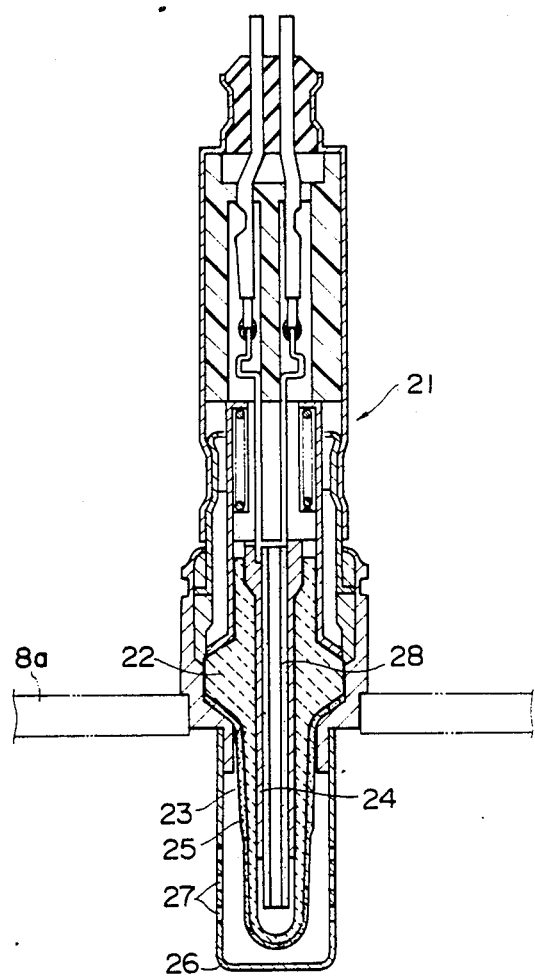
FIG. 2 is a longitudinal sectional view of an oxygen sensor fitted to the engine of FIG. 1 and shown in said figure, said oxygen sensor having a heater for keeping its sensor element at an appropriate operating temperature.

Referring to FIG. 2, the oxygen sensor 21 fitted in the wall 8a of the exhaust manifold 8 comprises a sensor element 22 formed as a tube with one end closed and made of a solid electrolyte material such as zirconia which can transmit oxygen ions. The outside of this sensor element 22 has, laid on it, an outer electrode 23 formed as a porous thin conducting layer (this layer is not clearly separately shown in the figure because it is so thin as to be represented by a single line), and the inside of said sensor element 22 has, likewise laid on it, an inner electrode 24 likewise formed as a porous thin conducting layer (again, this layer is shown only by a single line in FIG. 2). The outer surface of the outer electrode 23 has an exhaust gas dispersion layer 25 also laid on it, said layer 25 being formed of porous ceramic. The sensor element 22, etc., are mounted within a casing and so on, not particularly described here because they are per se known, and are fixed into the wall 8a of the exhaust manifold 8 with their lower parts in FIG. 2 projecting into the interior of said exhaust manifold 8. And a shield 26 with a plurality of holes 27 formed therein is provided around said lower ends of the sensor element 22 etc. projecting into the exhaust manifold 8, so as to protect them from the impact of the rushing flow of exhaust gases in the exhaust manifold 8, while allowing said exhaust gases to impinge gently on the exhaust gas dispersion layer 25 and the outer electrode 23 to reach the sensor element 22. During use of this oxygen sensor 21 as a current limiting type lean sensor, a certain voltage is applied by the control device 16 between the outer electrode 23 and the inner electrode 24, so that the current between these electrodes increases approximately in proportion to the oxygen concentration in the exhaust gases flowing through the exhaust manifold 8, within certain limits, as is per se well known. And, in order to keep the sensor element 22 etc, at the correct temperature for activation, an electrical heater 28 is provided for the oxygen sensor 21. This heater 28 is a per se known type of resistive heater, and the magnitude of the heating power instantaneously provided thereby is proportional to the product of the voltage and the amperage being provided by the control device 16 thereto.

The function of the control device 16 is in partial outline as follows. From the data it receives relating to engine rotational speed from the crank angle sensor 19 and relating to intake manifold pressure from the intake manifold pressure sensor 20, it determines the volume of intake air which is being sucked into the combustion chamber in each intake stroke of the piston 3, and according thereto determines a theoretically proper amount of fuel to be mixed with this intake air to provide a proper and appropriate target value for the air/fuel ratio of the air-fuel mixture in the combustion chamber. And, during normal engine operation when the engine 1 has been warmed up as is indicated by the output of the engine cooling water temperature sensor 35, based upon the actual value of the oxygen concentration in the exhaust gases in exhaust manifold 8 of the engine 1 as detected by the oxygen sensor 21, information regarding which is dispatched therefrom to the control device 16, said control device 16 makes a correction to this theoretical value in order to produce a value for the actual amount of fuel to be injected, so as to being the air/fuel ratio to its target value by a form of per se known feedback control. Then, the control device 16 produces electrical output signals at appropriate crank angles and supplies them to the solenoid 15a of the fuel injector 15, so as to control the opening and closing of the fuel injector 15 so as to inject this determined appropriate amount of fuel, in each injection spirt. On the other hand, when the engine 1 has not yet properly been warmed up as is again indicated by the output of the engine cooling water temperature sensor 35, no such feedback correction according to exhaust oxygen concentration of the calculated theoretically proper amount of fuel to be injected in order to provide a proper and appropriate target value for the air/fuel ratio of the air-fuel mixture in the combustion chamber is made, but instead the theoretically calculated value is directly used as a value of fuel to be injected, and accordingly the control of fuel injection is by a form of open loop control without any feedback. At this time the air/fuel ratio is controlled to be smaller than in the warmed up engine case when feedback is being utilized.

Figure 3:
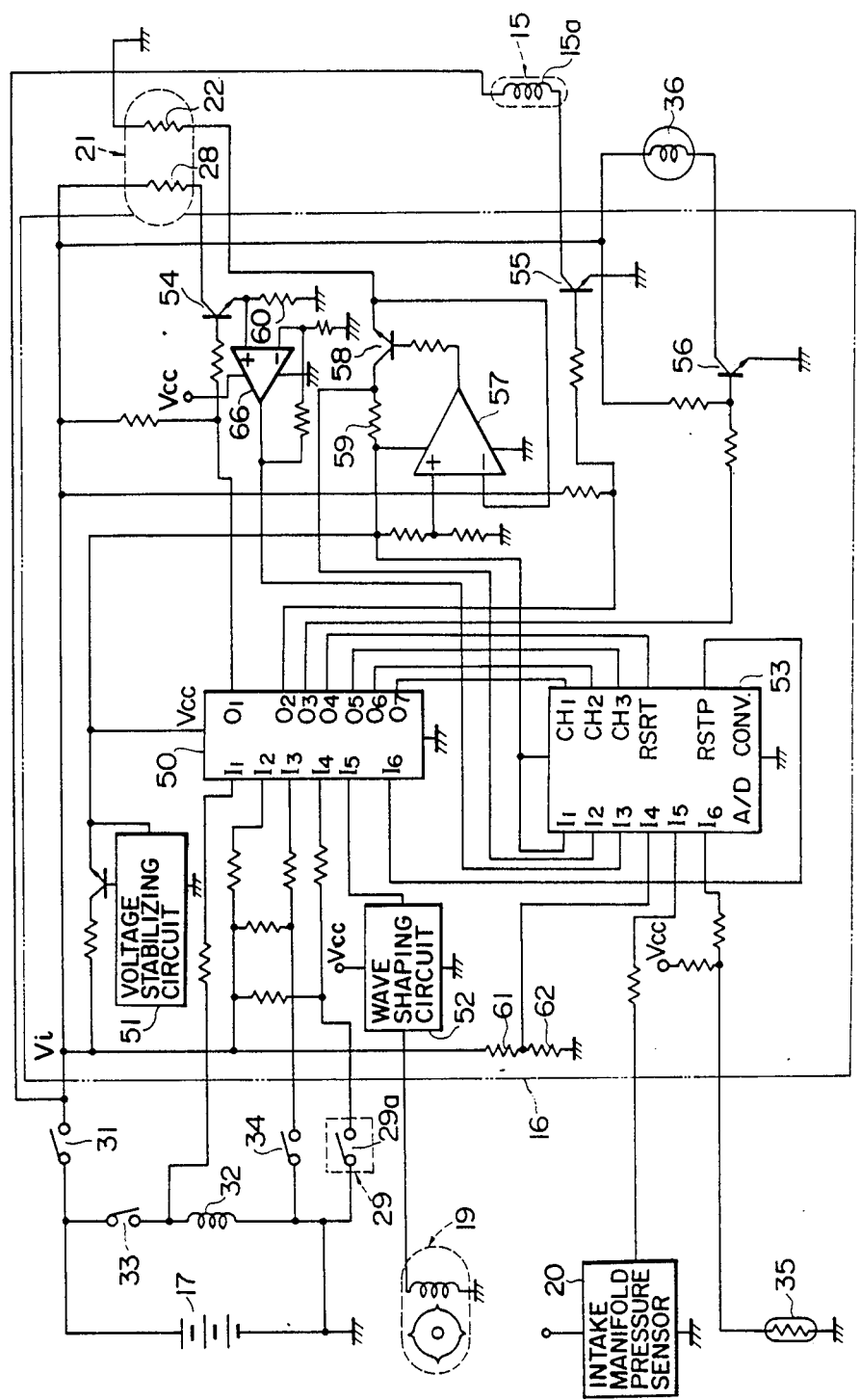
FIG. 3 is a partial circuit diagram of the preferred embodiment of the oxygen sensor heating control system of the present invention, and of various ancillary elements thereof, and particularly showing a microcomputer incorporated in said control system.

Referring to FIG. 3, herein the internal structure of the control device 16 is partially shown as an electrical circuit diagram, and also ancillary circuits relating thereto are shown. This control device 16 comprises a microcomputer 50, which may be for example of the Motorola 6801 type, and this microcomputer 50 is powered, like other parts of the circuitry of the control device 16, by a constant voltage Vcc supplied by a voltage regulator circuit 51 of a per se well known type, when and only when the ignition switch 31 of the vehicle is ON. This microcomputer 50 of this preferred embodiment has six inputs designated in the figure as I1 through I6 and seven outputs designated as O1 through O7. The inputs I1 through I6 are connected as follows. The input I1 receives an ON signal when and only when the starter switch 33 is in the ON state. The input I2 receives an ON signal when and only when the ignition switch 31 of the vehicle is in the ON state. The input I3 receives an ON signal when and only when the test switch 34 is in the OFF state. The input I4 receives an ON signal when and only when the switch 29a incorporated in the throttle valve idling opening amount sensor 29 is in the OFF state, i.e. when and only when the engine 1 is not idling. The input I5 receives the output of the crank angle sensor 19, after this has been converted to a square wave by a wave shaping circuit 52. And the input I6 receives a pulse width signal from a RSTP terminal of an A/D converter (an analog-digital converter) 53 of a per se well known sort. Further, the outputs O1 through O7 are connected as follows. The signals from the output O1 is furnished to the base of a transistor 54 as a pulse signal, so as to control the power supplied to the heater 28 of the oxygen sensor 21 as will be explained hereinafter. The signal from the output O2 is furnished to the base of a transistor 55 as a pulse signal, so as to control the solenoid 15a of the fuel injector 15 for providing fuel injection. The signal from the output O3 is furnished to the base of a transistor 56 as a sensor diagnostic result signal, so as to selectively energize the test alarm lamp 36 according to the result of circuit testing, as will be explained hereinafter. The signal from the output O4 is furnished to a convert control terminal RSRT of the A/D converter 53 as a convert start signal. And the signals from the outputs O5 through O7 are furnished as channel control signals to the channel control terminals CH1 through CH3 respectively of said A/D converter 53.

The transistor 54 receives the pulse signal from the output O1 of the microcomputer 50 at its base, and is thereby selectively switched ON so as to provide power via its collector to the heater 28 of the oxygen sensor 21, when and only when said pulse signal from said output O1 is ON. This power for the heater 28 is provided directly from the battery 17 via the ignition switch 31, i.e. not via the voltage regulation circuit 51. The transistor 55 receives the pulse signal from the output O2 of the microcomputer 50 at its base, and is thereby selectively switched ON so as to provide power via its collector to the solenoid coil 15a of the fuel injector 15, when and only when said pulse signal from said output O2 is ON. And the transistor 56 receives the signal from the output O3 of the microcomputer 50 at its base, and is thereby selectively switched ON so as to provide power via its collector to the test alarm lamp 36, when and only when said signal from said output O3 is ON. And the reference numeral 57 denotes a differential amplifier: when the ignition switch 31 is ON, then a constant voltage Vcc is provided via the voltage regulation circuit 51, and drives the transistor 58 to supply a constant voltage to the sensor element 22 of the oxygen sensor 21.

The A/D converter 53 comprises a multiplexer, not particularly shown, and is powered by the constant voltage Vcc supplied by the voltage regulator circuit 51. This A/D converter 53 of this preferred embodiment has six inputs designated as I1 through I6, as well as a control terminal RSRT and an output terminal RSTP and channels CH1 through CH3. The inputs I1 through I6 are connected as follows. The input I1 receives the reference voltage signal Vcc. The input I2 receives a voltage signal dropped from this reference voltage Vcc by a variable amount which depends upon the current through the sensor element 22 of the oxygen sensor 21 because of the resistor 59 as shown in the circuit diagram of FIG. 3. The input I3 receives a voltage signal amplified by a differential amplifier 66 from the voltage across a load dropping resistor 60, thus detecting the value of the current passing through the heater 28 of the oxygen sensor 21. The input I4 receives a voltage signal proportional to the current value of the voltage Vi being supplied by the battery 17, according to the operation of a voltage divider circuit incorporating two resistors 61 and 62. The input I5 receives a voltage signal representative of the pressure in the surge tank 10 of the engine intake system from the intake pressure sensor 20. And the input I6 receives a voltage signal representative of the temperature of the cooling water of the engine 1 from the engine cooling water temperature sensor 35.

Thus during operation by using a combination of the CH1 through CH3 signals from the microcomputer 50 a particular one of the input signals I1 through I6 is selected, and then, when the "start A/D convert" signal is dispatched by the microcomputer 50 (from its output O4) and is received at the RSRT terminal of the A/D converter 53, said A/D converter 53 performs the analog-digital conversion process and outputs a pulse width signal corresponding to the voltage of the selected input from its output terminal RSTP to the input I6 of the microcomputer 50. In particular, the microcomputer 50 receives pulse width signals from the A/D converter 53 which are together representative of the voltage across the current detecting resistor 59 for the sensor element 22 of the oxygen sensor 21, said signals being received by said A/D converter 53 at its I1 and I2 input terminals; and, by converting these pulse width signals into digital values and by subtracting one of them from the other, the microcomputer 50 can obtain a digital value representative of said voltage across said sensor element 22. This value, which is representative of the oxygen concentration in the exhaust gases flowing through the exhaust manifold 8, is the value that the microcomputer 50 used for performing the above described feedback control of the air/fuel ratio of the air-fuel mixture supplied to the engine 1, when appropriate.

Now, the operation of this preferred embodiment of the oxygen sensor heating control system of the present invention, while performing the preferred embodiment of the oxygen sensor heating control method of the present invention, will be explained with reference to FIGS. 4, 5, and 6, which are flow charts of the operation of certain parts of the program stored in the microcomputer 50.

Figures 4, 6:
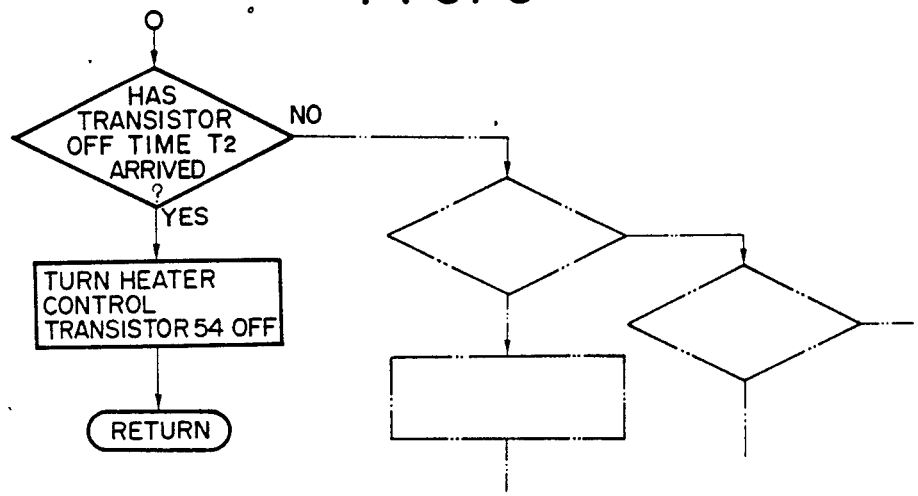
FIG. 4 is a flow chart of an initialization and base subroutine stored in the memory of the microcomputer of FIG. 3 and executed by it during the practice of said preferred embodiment of the oxygen sensor heating control method of the present invention.
FIG. 6 is a flow chart of a time compare interrupt subroutine also stored in the memory of the microcomputer of FIG. 3 during the practice of said preferred method embodiment.

The flow chart of FIG. 4 shows the operation of an initialization and base subroutine which is caused to be executed by the microcomputer 50 when the ignition switch 31 is turned on. The initialization part of this subroutine performs various operations such as register initialization and I/O port definition and so on, which the base part of this subroutine performs various operations such as calculating the fuel injection amount for feedback and the fuel injection amount cooling water temperature correction coefficient and so on.

Figure 5:
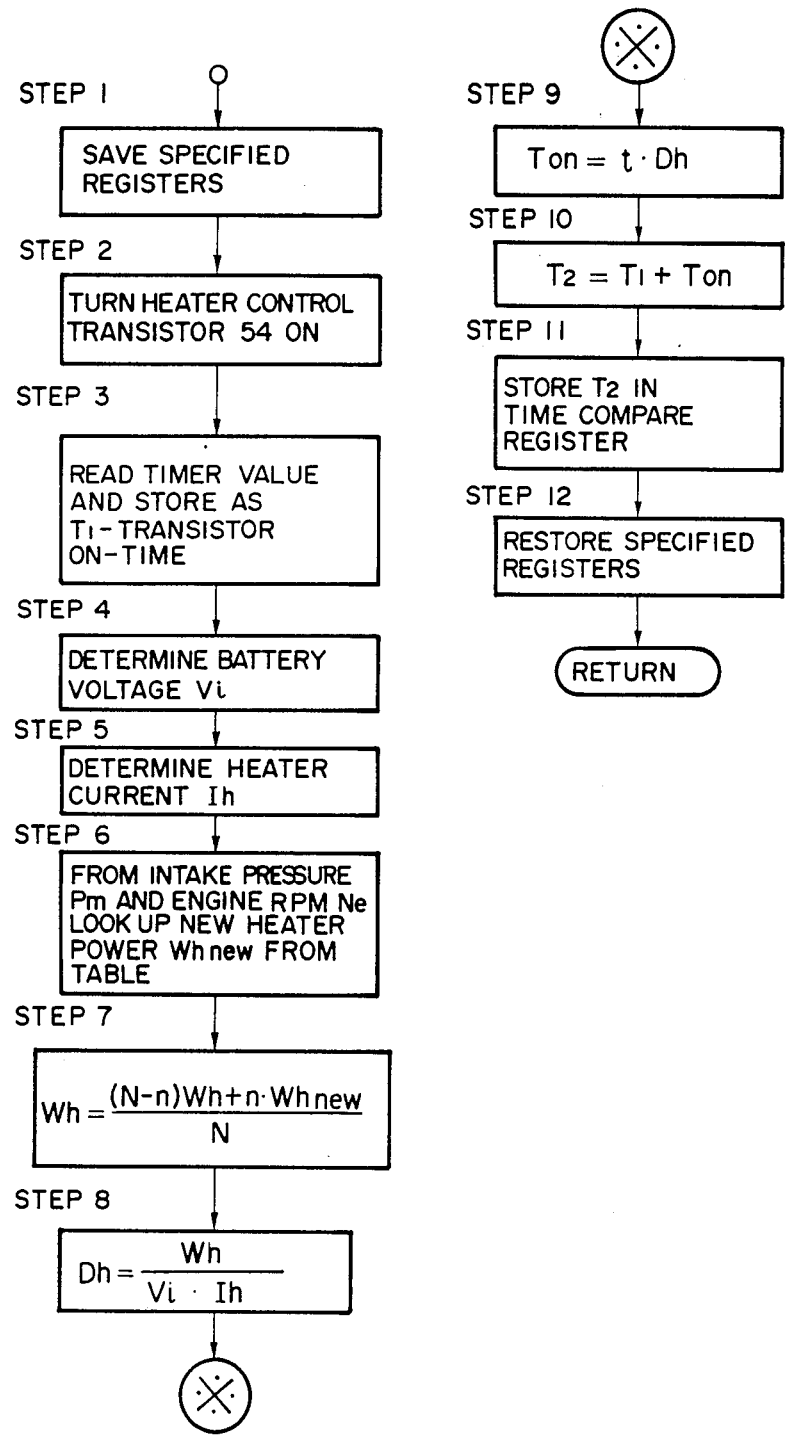
FIG. 5 is a flow chart of an interrupt subroutine for controlling supply of electrical energy to said oxygen sensor heater, stored in the memory of the microcomputer of FIG. 3 and executed by it at fixed intervals during the practice of said preferred method embodiment.

The flow chart of FIG. 5 shows the operation of an interrupt subroutine for controlling supply of electrical energy to the heater 28 of the oxygen sensor 21; and this subroutine is caused to be executed by the microcomputer 50 at fixed intervals, which are for example of the order of tens of milliseconds.

In this FIG. 5 subroutine, first, in the step 1, certain registers are saved.

Next, in the step 2, the heater control transistor 54 is turned ON, i.e. an ON signal is output to the base of the transistor 54 from the output O1 of the microcomputer 50. This starts to supply power to the heater 28, i.e. turns said heater 28 ON.

Next, in the step 3, the present count value of a free running timer attached to the microcomputer 50 is read, and is stored as T1, the ON time for the transistor 54.

Next, in the step 4, the value Vi of the battery voltage is determined by, as described above, selecting the input I4 of the A/D converter 53 (see FIG. 3), which receives a voltage representative of this battery voltage Vi. In this case, the A/D converter 53 sends an output pulse signal representative of the battery voltage Vi to the microcomputer 50. Also, similarly, in the next step 5, the value Ih of the current through the heater 28 is determined, by selecting the input I3 of the A/D converter 53, and by thus reading into the microcomputer 50 a pulse signal corresponding to the voltage drop across the resistor 60 on said input I3 of the A/D converter 53.

Next, in the step 6, first the current values of the intake manifold pressure Pm and the engine revolution speed Ne are determined by the microcomputer 50: the intake manifold pressure Pm is determined in a similar way to the determination of the battery voltage Vi and of the heater current Ih in the steps 4 and 5 by the microcomputer 50 selecting the input I5 of the A/D converter 53, and the engine revolution speed Ne is determined by calculating the time interval between successive pulses from the crank angle position sensor 19 supplied to the input terminal I5 of the microcomputer 50. Next, by consultation of a two way look up table of values stored in the ROM (read only memory) of the microcomputer 50, a proper and appropriate value for the amount $Wh_{new}$ of electrical power to be now supplied to the heater 28 of the oxygen sensor 21 is determined. This value of heater power stored in the table and designated herein as $Wh_{new}$ is determined on the assumption that no time delay is required to be incorporated in the calculation of the heater power supply amount, as explained earlier in this specification; in other words, on the assumption that these values of the engine operational parameters Vi, Ih, etc., are steady state values that have been maintained and will be maintained for a relatively long time. The values of heater power in this look up table in the ROM are typically determined in advance by experiment, and generally decrease as the intake pressure increases and as the engine revolution speed increases.

Next, in the step 7, the value of the actual amount of power Wh to be supplied to the oxygen sensor element heater 28 is calculated as a weighted average of the power currently being supplied to said heater 28, i.e. the value of this heater power Wh as determined in the previous iteration of this interrupt routine of FIG. 5, and the new desired value therefor $Wh_{new}$ determined in the previous step. The weights given to the present value of heater power Wh and to the new value therefor $Wh_{new}$ are, in the shown exemplary calculation, respectively designated as (N−n) and n, so that the calculation is done by calculating the value $(N-n)*Wh+n*Wh_{new})/N$, and by then assigning this value to Wh. As a typical example, the value of N may be 8 and the value of n may be 1, so that this calculation is performed by giving a weight of seven to one in favor of inertia for the value of Wh, i.e. by calculating $(7Wh+Wh_{new})/8$ and by assigning this value to Wh. Thereby, the actual value Wh of power supplied to the heater element 28 is made to track the desired value $Wh_{new}$ therefor with a certain time delay, i.e. with a certain inertia. As explained previously, this inertia, which is particularly according to the concept of the present invention, is desirable because of the time lag which is desirable in the alteration of power supply amount to the heater 28, when the operational conditions of the engine 1 alter abruptly, so as to correspond to the time lag which inevitably occurs in the alteration of the temperature of the exhaust gases of the engine 1. In any case, after the calculation of the actual heater power Wh in this step 7, the flow of control proceeds next to the step 8. By the way, since when the ignition switch 31 of the vehicle is turned off the value of Wh naturally disappears from the memory of the microcomputer 50 as it is deenergized, some predetermined value $Wh_{start}$ may be used at the restarting of the engine, on the first iteration of the routine of FIG. 5, said value $Wh_{start}$ being appropriately chosen, either as a constant, or as depending upon the temperature of the cooling water of the engine 1 upon initial starting up.

In this step 8, the duty ratio Dh of the power pulse signal to be supplied to the heater element 28 of the oxygen sensor 21, in order to obtain the correct desired (average) power supply value Wh, is calculated as the ratio of the desired power Wh and the power which would be dissipated in the heater element 28 if a continuous supply of power from the battery 17 were provided thereto—i.e. the product of the battery voltage Vi and the present heater current Ih. This duty ratio Dh decreases with increase in Ih, the current in the heater 28. Of course, the value Wh of the power supplied in this iteration of this routine remains set in the memory of the microcomputer 50 for reference in the next iteration, in the step 7 thereof, as explained above. Next, control passes to the step 9.

Next, in the step 9, from the heater control period t and the duty ratio Dh calculated as above, the length of time Ton that the heater 28 is to be energized is calculated as t.Dh. And next, in the step 10, the time point T2 at which the heater 28 should be deenergized is determined, as being T1+Ton.

Next, in the step 11, this time T2, at which the transistor 54 should be turned OFF and the heater 28 should be deenergized, is stored in a "time compare register" in the memory of the microcomputer 50.

Finally, in the step 12, the registers which were saved in the step 1 are restored; and then the subroutine returns.

The flow chart of FIG. 6 partially shows the operation of a time compare interrupt subroutine. In this subroutine, first a decision is made as to whether the transistor off time T2, stored in the aforesaid time compare register of the memory of the microcomputer 50 as explained in the step 12, has arrived or not. It should be understood that the time counter is upcounted at fixed time intervals. If the time point T2 has not yet arrived, then the flow of control is transferred to various other interrupt decisions and actions, as schematically indicated by the double dotted lines and boxes; but, if the time point T2 for switching off the heater power supply transistor 54 has in fact arrived, then the flow of control is transferred to a block which turns said heater control transistor 54 OFF by outputting to its base an OFF signal from the output O1 of the microcomputer 50. This stops supplying power to the heater 28, i.e. turns said heater 28 OFF. And then finally the subroutine returns.

Figure 8:
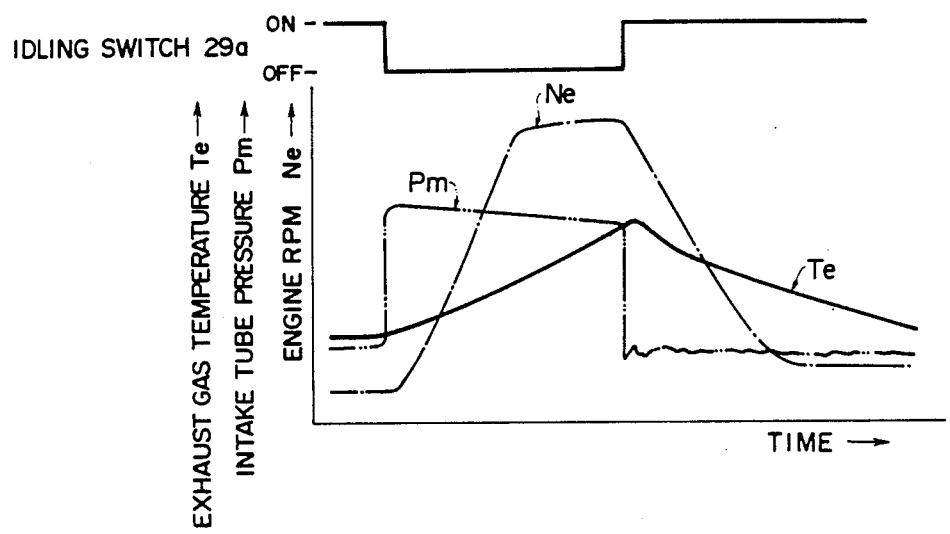
FIG. 8 is a graph showing, against time, the ON/OFF situation of an idle sensor switch of the system of FIGS. 1 through 3, the actual temperature of the exhaust gas of the engine to which said system is fitted, the pressure in the intake system of said engine, and the revolution speed of said engine.
Figure 9:
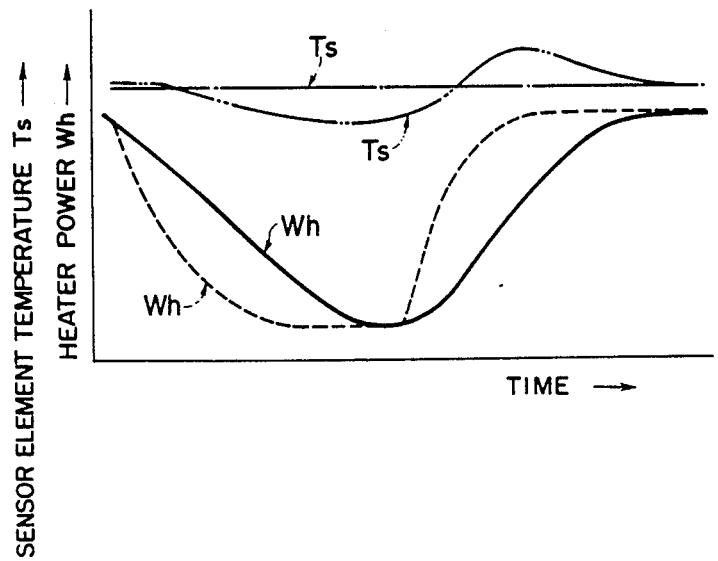
FIG. 9 is a graph showing, against time, the power supplied to the heater and the temperature of the sensor element of the oxygen sensor, both of these quantities being shown both in the case of the preferred embodiment of the present invention shown and described and also in the case of a typical prior art.

Thus, referring to FIG. 7, which is a timing chart showing the duty ratio control performed by the interrupt routine, and which shows against time the battery voltage Vi, the current Ih received by the heater 28, the ON/OFF signal to the heater control transistor 54, the Vi input timing, the Ih input timing, the timing of the calculation of duty ratio, the timing of the transistor-OFF signal, and the count value counted by the timer, the operation of the shown preferred embodiment of the present invention will be further clarified. The results of this operation are further shown by FIGS. 8 and 9. FIG. 8 is a time chart showing, against time, the ON/OFF situation of the idling switch 29a of the throttle opening sensor 29 in a typical operational episode, in which, from the accelerator pedal is depressed, then it is held depressed for a considerable time period, and then it is again allowed to raise and is not later depressed for another considerable time period. FIG. 8 also shows the variational behavior of the temperature Te of the exhaust gases of the engine during this operational episode, and the concurrent variational behavior of the intake tube pressure Pm and of the engine revolution speed Ne, which are used for calculation of the new heater power $Wh_{new}$ in the step 6 of the subroutine of FIG. 5. From this figure it is clear that, as explained above, generally change in the value of the exhaust gas temperature Te lags behind changes in the values of the intake tube pressure Pm and of the engine revolution speed Ne, thus justifying the time damped calculation of oxygen sensor heater power Wh performed according to the present invention as explained above. And, corresponding to this, FIG. 9 is a graph showing the behavior of the power Wh supplied to the heater element 28 against time, said heater power Wh being shown along the vertical axis and time being shown along the horizontal axis, both in the case of the present invention by the solid line and in the case of a typical prior art by the dashed line. This shows that in the case of the present invention the diminished application of heater power Wh, necessitated by the increase in throttle opening during this operational episode as explained previously, is somewhat delayed as compared to the operation of the prior art, thus more nearly corresponding to the increase in the temperature Te of the exhaust gases of the engine. FIG. 9 also shows the behavior of the temperature Ts of the sensor element of the oxygen sensor 21 against time, said sensor element temperature Ts being also shown along the vertical axis, both in the case of the present invention by the single dotted line and in the case of the aforementioned typical prior art by the double dotted line. Particularly by this pair of graphs, it is clear that the temperature of the oxygen sensor element itself is kept much more uniform as engine operational parameters change, in the case of the present invention, than in the case of the prior art. Accordingly, it is seen that, according to the method and the system of the present invention, the power dissipated by the heater is, by the smoothing performed on it, caused to time-behave similarly to the response of exhaust gas temperature to change in the operational parameters of the engine. Accordingly, according to this method and system, such control of the power supplied to the oxygen sensor heater is performed, as to ensure that the oxygen sensor is kept at a proper temperature at all times. In particular, such a control of the oxygen sensor heater is performed, as to ensure a proper temperature for the oxygen sensor, particularly when engine operational parameters change abruptly. Further, it is particularly avoided that upon rapid increase of engine load the temperature of the sensor element should be allowed to drop; and, similarly, it is particularly avoided that upon rapid decrease of engine load the temperature of the sensor element should be allowed to rise. Thus, no risk is run of overheating the heater element of the oxygen sensor heater, or of placing unnecessary stress on the heater element of the oxygen sensor heater, or of causing damage thereto. This, therefore, maintains the reliability of the heater element of the oxygen sensor heater and of the apparatus as a whole. Further, it is prevented that during quick variation of operational parameters of the engine the quality of the exhaust emissions of the engine should be poor, that the drivability of the engine should be poor, or that during so called "hot soak" the oxygen sensor element should be unduly heated up.

Although the present invention has been shown and described with reference to the preferred embodiment thereof, and in terms of the illustrative drawings, it should not be considered as limited thereby. Various possible modifications, omissions, and alterations could be conceived of by one skilled in the art to the form and the content of any particular embodiment, without departing from the scope of the present invention. For example, although in the shown preferred embodiment the parameters according to which the fuel injection amount for the engine, and the amount of heater power provided for the oxygen sensor element heater, were engine intake manifold pressure and engine revolution speed, the present invention is not limited to this choice of parameters, and for example engine intake air flow and engine revolution speed could be utilized instead; other variations, such as throttle opening, are also possible for the chosen parameters. Also, although in the shown preferred embodiments of the method and device of the present invention the weighted average of the presently calculated value and certain previous values for the power to be supplied to the oxygen sensor heater in fact was only a weighted average involving said present value and the most recent previous value, in fact in other embodiments more remotely previous values could also be included in this average. Other possible functions for deriving the actual value of the power to be supplied to the heater from the target value calculated therefor and the previous values could also be conceived of. Therefore it is desired that the scope of the present invention, and of the protection sought to be granted by Letters Patent, should be defined not by any of the perhaps purely fortuitous details of the shown preferred embodiment, or of the drawings, but solely by the scope of the appended claims, which follow.

What is claimed is:

1. In an internal combustion engine having an exhaust system and an oxygen sensor fitted to the exhaust system, the oxygen sensor including a sensor element and an electrically-powered heater for heating same, a method for controlling the electrical supply to the heater, comprising the steps of:

storing the existing value of the power supplied to the heater;

determining a target value for power to be supplied to the heater at a future time when the temperature of the engine exhaust gases reflects values consistent with engine operating parameters;

delaying the application of the full value of said target value until said future time; and recycling to said storing step.

2. The method of claim 1, wherein said delaying step includes the steps of:

calculating an interim value of power to be applied to the heater, said interim value being intermediate between said existing power value and said future power value; and applying said interim power value to the heater.

3. The method of claim 2, wherein said interim power value is calculated by adding the product of said existing power value and a first weighting factor to the product of said future power value and a second weighting factor, and dividing the resulting sum by the sum of said first and second weighting factors.

4. The method of claim 3, wherein said first weighting factor is larger than said second weighting factor.

5. In an internal combustion engine having an exhaust system and an oxygen sensor means fitted to the exhaust system for controlling the fuel/air ratio provided to the engine, wherein the oxygen sensor includes a sensor element and an electrically-powered heater for heating same, a method for controlling the electrical supply to the heater, comprising the steps of:

storing the existing value of the power supplied to the heater;

determining a target value for future power to be supplied to the heater, based upon engine intake pressure and speed;

delaying the application of the full value of said target value for a time period sufficient to allow the temperature of the engine exhaust gases to reflect values consistent with said engine intake pressure and speed, said delaying step including the steps of:

calculating an interim power value by adding the product of said existing power value and a first weighting factor to the product of said future power value and a second weighting factor, and dividing the resulting sum by the sum of said first and second weighting factors, said first weighting factor being larger than said second weighting factor and selected such that said delay time period is sufficiently long to allow said exhaust gas temperature to reflect said engine intake pressure and speed;

applying said interim power value to the heater; and recycling to said storing step.

* * * * *

UNITED STATES PATENT AND TRADEMARK OFFICE
CERTIFICATE OF CORRECTION

PATENT NO. : 4,694,809

DATED : Sep. 22, 1987

INVENTOR(S) : Nakano et al.

It is certified that error appears in the above-identified patent and that said Letters Patent is hereby corrected as shown below:

Column 2, line 26: "change" should be -- change, --

Column 3, line 6: "thereof" should be -- thereto --

Column 3, line 64: "or damage" should be -- or cause damage --

Column 6, line 38: "now show" should be -- not shown --

Column 7, line 48: "he" should be -- the --

Column 10, line 60: "used" should be -- uses --

Column 11, line 9: "which" should be -- while --

Column 13, line 37: "pedal is" should be -- pedal of the vehicle not being substantially depressed, first said accelerator pedal is --

Column 13, line 39: "raise" should be -- rise --

Signed and Sealed this

Twenty-sixth Day of April, 1988

Attest:

DONALD J. QUIGG

Attesting Officer

Commissioner of Patents and Trademarks